United States Patent
Höhse et al.

(10) Patent No.: US 11,584,911 B2
(45) Date of Patent: Feb. 21, 2023

(54) SPECTROSCOPY CELL IN OR ON AN OUTER WALL OF A CONTAINER AND SPECTROSCOPY METHOD

(71) Applicant: Sartorius Stedim Biotech GmbH, Göttingen (DE)

(72) Inventors: Marek Höhse, Göttingen (DE); Christian Grimm, Heiligenstadt (DE)

(73) Assignee: Sartorius Stedim Biotech GmbH

( * ) Notice: Subject to any disclaimer, the term of this patent is extended or adjusted under 35 U.S.C. 154(b) by 1071 days.

(21) Appl. No.: 16/319,124

(22) PCT Filed: May 4, 2017

(86) PCT No.: PCT/EP2017/000559
§ 371 (c)(1),
(2) Date: Jan. 18, 2019

(87) PCT Pub. No.: WO2018/014984
PCT Pub. Date: Jan. 25, 2018

(65) Prior Publication Data
US 2020/0208094 A1  Jul. 2, 2020

(30) Foreign Application Priority Data

Jul. 19, 2016  (DE) .................... 10 2016 008 826.5

(51) Int. Cl.
*C12M 1/00* (2006.01)
*C12Q 1/02* (2006.01)
*G01N 21/01* (2006.01)

(52) U.S. Cl.
CPC ............ *C12M 41/06* (2013.01); *C12M 31/00* (2013.01); *C12Q 1/02* (2013.01); *G01N 21/01* (2013.01)

(58) Field of Classification Search
CPC ......... C12M 41/06; C12M 31/00; C12Q 1/02; G01N 21/01
See application file for complete search history.

(56) References Cited

U.S. PATENT DOCUMENTS 4,461,845 A  7/1984 Dessau et al.
5,750,998 A  5/1998 Goldman
(Continued)

FOREIGN PATENT DOCUMENTS

DE  10 2010 007559  8/2011
DE  20 2012 004503  5/2012
(Continued)

OTHER PUBLICATIONS

International Search Report and Written Opinion, dated Jul. 21, 2017, from PCT Patent Application No. PCT/EP2017/000559, 15 pages.

*Primary Examiner* — Michael A Lyons
*Assistant Examiner* — Omar H Nixon
(74) *Attorney, Agent, or Firm* — Klarquist Sparkman, LLP

(57) ABSTRACT

One aspect relates to a bioreactor and/or mixing container that includes an outer wall and a spectroscopy cell arranged in and/or on the outer wall. The spectroscopy cell includes a first optical area and a second optical area arranged opposite the first optical area. The first optical area and the second optical area can be set at at least two different distances from one another. A specimen-receiving area is located between the first optical area and the second optical area.

18 Claims, 6 Drawing Sheets

(56) References Cited

U.S. PATENT DOCUMENTS

| | | | | |
|---|---|---|---|---|
| 7,910,065 B2* | 3/2011 | Clark | ................ | G01N 33/5008 |
| | | | | 435/7.1 |
| 2013/0011862 A1* | 1/2013 | Rodriguez Albalat | ...................... | |
| | | | | G01N 33/54346 |
| | | | | 435/7.37 |
| 2013/0039810 A1* | 2/2013 | Riechers | ................ | C12M 41/02 |
| | | | | 422/82.05 |

FOREIGN PATENT DOCUMENTS

| | | |
|---|---|---|
| EP | 0 145 877 A2 | 6/1985 |
| JP | S58 68645 A | 4/1983 |
| JP | H10 115590 A | 5/1998 |
| WO | WO 03/102288 A1 | 12/2003 |
| WO | WO 2013/174448 A1 | 11/2013 |

* cited by examiner

SPECTROSCOPY CELL IN OR ON AN OUTER WALL OF A CONTAINER AND SPECTROSCOPY METHOD

CROSS REFERENCE TO RELATED APPLICATIONS

This is the U.S. National Stage of International Application No. PCT/EP2017/000559 filed May 4, 2017, which in turn claims the benefit of German Patent Application No. 10 2016 008 826.5, filed Jul. 19, 2016. German Patent Application No. 10 2016 008 826.5 is incorporated herein in its entirety.

DESCRIPTION

The invention relates to a container, in particular a bioreactor and/or mixing container, in the outer wall of which a spectroscopy cell is arranged, a corresponding spectroscopy cell, and a spectroscopy method for a container.

Previously known spectroscopy measuring cells for containers, in particular for bioreactor and/or mixing containers, largely use costly optically transparent windows such as sapphire glass and/or quartz glass, wherein two opposing windows enclose a medium to be studied. For the purpose of a spectroscopic measurement of the medium in the container, the optical windows and the medium arranged therebetween are illuminated and a spectrum resulting therefrom is registered. However, the measuring cells known from the prior art have proven to be unsuitable for single-use applications, i.e., for one-time use, since the optical windows represent a significant cost factor in the production and are only reusable with great effort.

In addition, in the known spectroscopic measuring cells, no validation of the spectroscopic measurement and/or the overall measuring system can take place during the measuring process, since no reference or reference medium can be introduced into the measuring gap between the two optical measuring areas. Furthermore, a spectroscopic measurement through the outer wall and/or bag film of the container is usually precluded because of the lateral variations of the optical properties of the outer wall and/or the bag film.

A further disadvantage in the case of the use of known optical spectroscopy cells is the fixed specification of the optical path length (i.e., the distance between two opposing optical windows) at the production time and/or a lack of possible variation of the optical path length during the measurement process.

It is therefore the object of the present invention to enable a cost-effective spectroscopic measurement for containers, in particular bioreactor and/or mixing containers, which enables high accuracy.

This object is achieved by the features of the independent claims. Preferred embodiments are defined in the dependent claims.

One aspect relates to a container, in particular a bioreactor and/or mixing container, comprising:
an outer wall designed to enclose a medium; and
a spectroscopy cell, which is arranged in and/or on the outer wall, wherein the spectroscopy cell comprises:
a first optical area;
a second optical area arranged opposite to the first optical area, wherein the first optical area and the second optical area can be set at at least two different distances from one another; and
a specimen space located between the first optical area and the second optical area, wherein, at a measuring distance of the at least two different distances, the specimen space can be filled with the medium and wherein, for the purposes of carrying out a spectroscopic measurement, at least one optical area has a light-transmissive embodiment.

It is therefore advantageously possible to vary or set an optical path length between the two optical areas. Furthermore, it is advantageously possible for the acquisition of a spectrum having high quality to set an optimum optical path length between the two optical areas, in particular as a function of the employed wavelength of the illuminating light and as a function of an absorption and/or scattering of differing strengths of the light.

The outer wall of the container, in particular of the bioreactor and/or mixing container, can be designed to enclose a medium. The medium can comprise, for example, fluids and/or cell cultures or the like. The side of the outer wall which encloses the medium can be considered to be an inner side of the outer wall. Accordingly, the outer side of the outer wall can be considered to be the side which does not enclose a medium and/or is arranged opposite to the inner side of the outer wall. The outer wall of the container, in particular of the bioreactor and/or the mixing container, can be embodied as rigid and/or flexible. In other words, the outer wall of the container, in particular of the bioreactor and/or mixing container, can be embodied as deformable or also not deformable. In addition, the outer wall of the container, in particular of the bioreactor and/or mixing container, can be embodied such that two opposing regions on the inner side of the outer wall of the container cannot be brought together. In other words, the outer wall of the container can be embodied so it is at least partially not completely compressible.

Furthermore, the container, in particular the bioreactor and/or mixing container, can be embodied as a disposable container, i.e., for one-time use. Furthermore, the container, in particular the bioreactor and/or mixing container, can be suitable for carrying out a bioprocess.

The spectroscopy cell arranged in and/or on the outer wall can have a connecting area, which is connectable to the outer wall of the container. A connection of the spectroscopy cell to the outer wall of the container can be performed, for example, by welding and/or adhesive bonding of the connecting area to the outer wall of the container. The connection of the spectroscopy cell to the outer wall of the container can be embodied as detachable. For example, the adhesive bond can be detached and/or a screw-on connection can be provided. It is thus possible to reuse the spectroscopy cell after cleaning.

The optical areas arranged opposite one another (in particular approximately plane-parallel), i.e., the first optical area and the second optical area, can in particular be able to be arranged at different distances from one another. Thus, for example, the distance between the first optical area and the second optical area can be essentially zero (0 mm), so that the first optical area (at least partially or in regions) is arranged and/or abuts on the second optical area. The space spanned by the distance between the first optical area and the second optical area can be embodied and/or can be used as a specimen space. The specimen space can be designed to accommodate a medium and/or a part of the medium which is enclosed by the outer wall of the container. A medium to be measured can therefore be arranged between the first optical area and the second optical area.

In particular, the optical areas can be embodied as active and/or inactive optical elements and/or areas. Thus, for example, the optical areas can be embodied as light-transmissive or transparent and/or reflective. In particular, an optical area embodied as light-transmissive or transparent can be on average at least approximately 30% transparent or light-transmissive over the range to be detected. An area embodied as reflective can be designed to reflect light in the provided wavelength range at least 30% on average.

Furthermore, the optical areas can be embodied as optically active (for example, lenticular), for example, to enable focusing of the emitted light onto a specific point, for example, onto a detection means arranged on the optical area and/or onto an optical fiber arranged on or close to the optical area.

A setting element can be embodied or provided to set the distance between the first optical area and the second optical area. The setting element is designed in particular for the purpose of moving or displacing the first optical area in the direction toward the second optical area and/or away from the second optical area. Alternatively or additionally, the setting element can be designed for the purpose of moving or displacing the second optical area in the direction toward the first optical area and/or away from the first optical area. In other words, the setting element can be designed for the purpose of moving or displacing both optical areas in relation to one another (i.e., toward one another and/or away from one another). The setting element is designed in particular such that the setting element is operable manually or automatically, for example, via a stepping motor. Furthermore, the distance between the first optical area and the second optical area can in particular be set in a reproducible or repeatable manner. In other words, a defined or specific (predetermined or pre-determinable) distance between the two optical areas can be set or set again in particular at any point in time in the measurement process.

By setting the distance between the first optical area and the second optical area, an optimum optical path length of the spectroscopy cell can therefore advantageously be specified, which takes into consideration an employed wavelength of the spectroscopic measurement and an absorption and/or scattering caused by the medium to be studied and/or by the optical areas.

The container preferably has a reference distance of the at least two different distances, in which the first optical area and the second optical area are arranged with respect to one another or in particular abut one another.

To carry out a spectroscopic measurement, for example, one optical area (for example, first optical area) can be illuminated with a light in the direction toward the opposing optical area (for example, second optical area) and a medium possibly arranged between the optical areas. The light exits again in particular at the opposing optical area, wherein a resulting spectrum can be supplied to a detection means (for example, comprising a spectroscope) and can be detected thereby.

For example, a suitable detection means can be provided at a light exit side of the opposing optical area (for example, second optical area), at which the light input or incident at the opposing optical area exits. For example, an optical fiber and/or a CCD chip for detecting the resulting spectrum can be arranged at the light exit side. In this case, the spectroscopic measurement can take place both in a distance or state in which the two optical areas (at least partially or in regions) abut one another, i.e., the distance between the two optical areas is essentially zero (0 mm), and also in a predefined distance not equal to zero of the two optical areas in relation to one another. In the case of an optical measurement in an assumed reference distance, at which the two optical areas in particular abut one another, i.e., the distance is zero and therefore essentially no medium is located between the optical areas, the spectroscopic measurement represents the optical properties of the two optical areas and can therefore be used as a reference spectrum.

For the case in which the two optical areas are spaced apart from one another, the result of the spectroscopic measurement comprises both the spectrum of the two optical areas and also the spectrum of the medium located and/or arranged in the specimen space.

The first optical area and the second optical area can preferably be embodied as essentially light-transmissive (in particular transparent or translucent), specifically at least for the wavelengths or radiations used during the spectroscopic measurement. In this case, the spectroscopic measurement can take place through the first optical area, a medium possibly located in the specimen space arranged therebetween, and the second optical area and/or the other way around. In this case, light from a first light source can be input or incident in the first optical area in the direction of the second optical area. On a side of the second optical area which faces away from the first optical area, the resulting spectrum can be detected (in particular directly or by means of interconnection of optical elements). In the case in which the two optical areas are located at a reference distance in relation to one another, i.e., in particular at least partially abut one another, the resulting spectrum solely contains or corresponds to the properties of the two optical areas.

Alternatively, one of the two optical areas can be embodied as light-transmissive (in particular transparent or translucent), specifically at least for the wavelengths used during the spectroscopic measurement, and the other optical area can be embodied as reflective, specifically at least for the wavelengths used during the spectroscopic measurement. In this case, light can be input or incident in the optical area embodied as light-transmissive in the direction of the optical area embodied as reflective. The input or incident light is reflected on the optical area embodied as reflective in the direction of the optical area embodied as light-transmissive. The resulting spectrum can be detected on a side of the optical area embodied as light-transmissive which faces away from the optical area embodied as reflective. The optical area embodied as reflective can also be embodied as the light-transmissive optical area, wherein a reflector element or film is arranged on the side facing away from the optical area embodied as light-transmissive.

The spectroscopy cell can preferably comprise illuminants and/or light sources, which can be coupled to the first optical area and/or second optical area. Furthermore, the spectroscopy cell can comprise detection means, which can be coupled to the first optical area and/or second optical area.

The illuminants which can be coupled to the first optical area and/or second optical area can be designed for the purpose of illuminating the opposing optical areas and a medium possibly located in the specimen space arranged therebetween. In particular, the illuminant can be embodied so it can be coupled to one side of an optical area which faces away from an opposing optical area. Furthermore, the optical illuminant can be embodied so it can be coupled directly or indirectly to the first optical area and/or second optical area.

For the case of substantially direct coupling, the illuminant can be embodied as directly abutting (or at a slight distance) on the corresponding optical area. In the case of an indirect coupling, an (optical) connecting element can be provided, which is embodied so it can be coupled both to the illuminant and also to the first and/or second optical area.

For example, one or more optical fibers can be provided as the connecting element, which optically couples or couple the illuminant to one of the optical areas. The optical fiber(s) can transport the light input or incident from the illuminant in the direction of the coupled optical area. The illuminant can be embodied, for example, as a diode and/or laser.

Furthermore, the detection means can be embodied so it can be coupled directly or indirectly to one of the optical areas. For example, in the case of a direct coupling, the detection means can be embodied so it can be coupled directly (or at a slight distance) on one side of an optical area, which faces away from the other optical area. The spectroscopy cell (in particular in the case of indirectly embodied coupling of the detection means to one of the optical areas) can preferably have a connecting element for connecting the detection means to one of the optical areas. An optical detector, for example, a photocell or a CCD chip, can be used, for example, as the detection means.

The embodiment of the illuminant and/or the detection means so they can be coupled is advantageous, since the illuminant and/or the detection means are thus reusable in particular. This is advantageous in particular in the case of single-use bioreactors, which are typically disposed of after one use. Furthermore, a coupling of the detection means outside a sterile region of the bioreactor is possible, so that preferably an ability to sterilize the detection means is not important.

The spectroscopy cell can preferably have at least one feedthrough, which is designed for the purpose of guiding the connecting element from an inner side of the container to an outer side of the container.

One of the optical areas can be arranged inside the container, in particular inside the bioreactor and/or mixing container. To couple this optical area arranged inside the container to an illuminant arranged outside the container and/or to a detection means arranged outside the container, the corresponding connecting element can be guided through the feedthrough. The connection between feedthrough and connecting element or the contact closure between feedthrough and connecting element is embodied as leak-tight and/or sealed, so that medium located in the container cannot escape through the feedthrough. Furthermore, the feedthrough is embodied such that a sterility of the interior of the container is ensured.

Furthermore, the connecting element can be embodied so it can be coupled both to an illuminant and also to a detection means. In other words, a connecting element can be embodied such that it can couple and/or connect an optical area alternately both to the illuminant and also to the detection means. As described above, the connecting element can be embodied as optical fiber(s). The optical fiber(s) can be embodied, for example, as monomodal or multimodal fiber(s) and/or can comprise multiple fiber bundles. In this case, one fiber bundle of the optical fiber can be designed to couple and/or connect the illuminant to an optical area. A further fiber bundle of the optical fiber can be designed to couple and/or connect the detection means to the optical area.

For the last-mentioned case, the other optical area, i.e., the optical area which is coupled neither to the illuminant nor to the detection means, can preferably be embodied as reflective and the first optical area, which is coupled to the illuminant and the detection means, in particular via the connecting element, can be embodied as light-transmissive. The medium located between the optical areas can also act as a reflector and/or the emitted wavelength and/or radiation can propagate in all spatial directions.

The spectroscopy cell can preferably be welded and/or adhesively bonded to the bioreactor container. For this purpose, a corresponding connecting area is provided on the spectroscopy cell and on the bioreactor container. The connecting area of the bioreactor container and the connecting area of the spectroscopy cell can be, for example, thermally welded and/or adhesively bonded. In addition, the spectroscopy cell can also be embodied as connectable to other devices, for example, to hoses, or the spectroscopy cell can be provided as a retrofitting article.

Furthermore, the spectroscopy cell can be provided sterile. This means the interior of the bioreactor container is not contaminated by the connection of the spectroscopy cell to the bioreactor container. Therefore, when the spectroscopy cell is provided in and/or on the bioreactor container, no contamination of the medium arranged in the bioreactor container takes place. Alternatively or additionally, the bioreactor provided with the spectroscopy cell can be (pre-) sterilized, for example, by means of gamma radiation.

The first optical area and/or the second optical area can preferably be manufactured from light-transmissive material (for example, glass, quartz, sapphire, and/or a polymer). Therefore, materials such as sapphire glass and/or quartz glass can be dispensed with by the determination of a reference spectrum of the first optical area and the second optical area. The spectroscopy cell can therefore be manufactured cost-effectively due to the cost advantage of normal glass and/or polymer compounds in relation to materials such as sapphire glass and/or quartz glass.

A further aspect relates to a spectroscopy cell for a (and/or connectable to a) container, in particular for a container according to the above aspect of one embodiment thereof, comprising:

a first optical area a second optical area arranged opposite to the first optical area, wherein the first optical area and the second optical area can be set at at least two different distances from one another; and a specimen space located between the first optical area and the second optical area, wherein, at a measuring distance of the at least two different distances, the specimen space can be filled with the medium and wherein, for the purposes of carrying out a spectroscopic measurement, at least one optical area has a light-transmissive embodiment.

The spectroscopy cell can furthermore comprise a connecting region and/or connecting area, which is designed for the purpose of connecting the spectroscopy cell to a container, in particular a bioreactor and/or mixing container. The connection of the spectroscopy cell to the container can be performed, for example, by welding and/or adhesive bonding. In this case, the connecting area of the spectroscopy cell is connected to a corresponding connecting area of the container and/or a corresponding recess in the outer wall of the container.

In addition, the spectroscopy cell can also be embodied as reusable. For this purpose, the connection between the container and spectroscopy cell can be embodied as detachable. After a first use of the spectroscopy cell, it is therefore possible to detach the spectroscopy cell from the container in order to reuse it after cleaning.

A further aspect relates to a spectroscopy method for a container, in particular in a bioreactor and/or mixing container, in particular using the container according to the above aspect or an embodiment thereof, comprising:

providing a spectroscopy cell in a wall of a container, in particular of a bioreactor and/or mixing container;

setting a reference distance of two optical areas of the spectroscopy cell;

registering a reference spectrum of the two optical areas;

setting at least one measuring distance between the two optical areas, wherein a medium to be studied is arranged between the optical areas;

registering at least one measurement spectrum of the two optical areas and the medium located therebetween; and ascertaining a spectrum of the medium based on the reference spectrum and the measurement spectrum.

Furthermore, the method can provide assuming and/or setting further measuring distances between the first optical area and the second optical area. In each case a spectrum of the first optical area, the second optical area, and a medium possibly arranged therebetween can be measured and/or detected at each of these set measuring distances between the first optical area and the second optical area. In other words, by setting further measuring distances, different path lengths can be detected, whereby the dynamic range of the spectroscopy cell can be substantially expanded. Thus, for example, long path lengths can be selected in the case of low concentration of the medium and short path lengths can be selected in the case of high concentrations of the medium. Scattering parameters can also be registered better by the measurement of different path lengths.

Furthermore, the method can provide in particular repeating the spectroscopic measurement at any arbitrary point in time and/or with defined distances between the optical areas. The method therefore enables a continuous referencing of the optical areas and/or the entire optical path length. An obtained spectrum, which includes the spectral component of the medium and the optical areas, can therefore be corrected by the reference spectrum, which only includes the spectral component of the optical areas. In addition, the optimum path length can be set between the optical areas at any method point in time for any arbitrary wavelength. The medium to be measured may therefore be supplied to a suitable spectroscopic examination and the spectroscopy cell can be adapted to the optimum measuring parameters, for example, required wavelength of the aluminate.

DESCRIPTION OF THE FIGURES

A preferred embodiment of the bioreactor container and/or the spectroscopy cell will be explained by way of example hereafter on the basis of the appended drawings. Although individual embodiments are described separately, individual features thereof can be combined to form further embodiments. In the figures:

FIGS. 1a and 1b show a perspective view of a spectroscopy cell 1, which is connectable to a bioreactor 100 (cf. FIG. 5b) as an example of a container according to one preferred embodiment of the invention.

The bioreactor 100 can be in particular a single-use system for biotechnological applications, a cross-flow system, a filtration system, a bioreactor container, a biogas system, a mixer or mixing system, a shaker, a freezing and thawing container, a device for the treatment of fluids, and/or similar systems. Furthermore, the bioreactor 100 comprises in particular the container or bioreactor container, in which specially cultivated microorganisms and/or cells are cultivated under the most optimum possible control conditions in a nutrient medium, in order to obtain either the cells themselves, parts thereof, and/or one of their metabolic products. For this purpose, one or more supply and/or discharge lines for the respective individual products or materials are required. Solid (biomass), liquid (nutrient medium), and/or gaseous (for example, air, oxygen, carbon dioxide, nitrogen) phases can especially be processed in the bioreactors. To ensure optimum conditions, typically one or more (different) parameters are measured and/or monitored in the interior of the bioreactor with the aid of sensors, which protrude into the interior of the bioreactor. Possible parameters to be measured are, for example, the pH value, the $O_2$ value, and the temperature of the medium or fluid contained in the bioreactor. In particular, spectroscopic measurements, for example, optical-spectroscopic measurement in absorption, transmission, transflection, fluorescence, and/or scattering are carried out in the ultraviolet (UV, at wavelengths from approximately 10 nm-400 nm), visible light (VIS, at wavelengths from approximately 400 nm-700 nm), near infrared (NIR, at wavelengths from approximately 0.78-3 μm), or middle infrared (MIR, at wavelengths from approximately 3-50 μm) spectral range inside the bioreactor container, which enable inferences about the medium (for example, the microorganisms and/or cells) and/or fluid contained therein and/or its state. If parameters should deviate from predefined optimum values, the deviations can be corrected by means of suitable measures. Bioreactors can be designed for multiple uses or as a disposable bioreactor. If it is a disposable bioreactor, they are frequently already manufactured at the factory together with one or more sensor(s) (for example, at least one spectroscopy cell 1), which are subsequently supplied as a sterile unit to the user. After use of the disposable bioreactor, the sensor (or at least parts thereof) can be disposed of together with the bioreactor. The sensor is therefore in particular a disposable sensor. However, it is also possible to provide the sensors so it can be coupled to a nonsterile region of the bioreactor, so that it can be coupled later to the sterile bioreactor and/or removed if needed without disrupting the sterility.

Figure 3A:
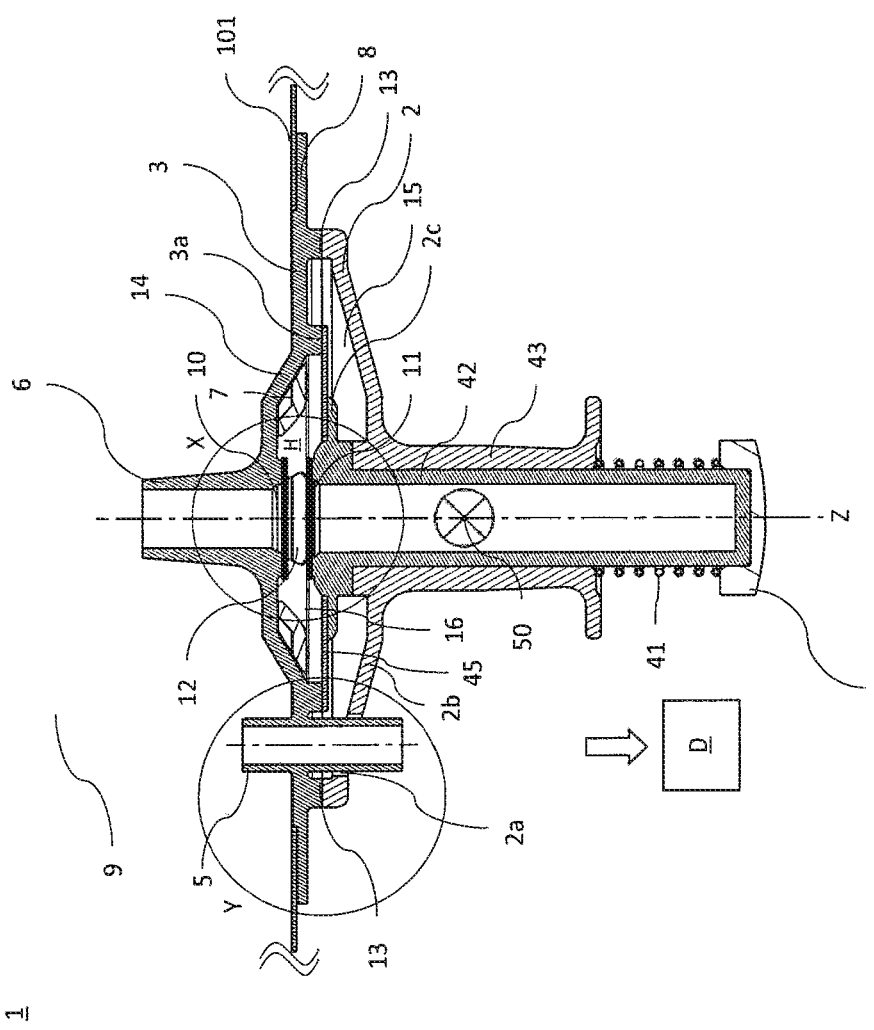
FIG. 3a shows a longitudinal section through the spectroscopy cell along the section line A-A' shown in FIG. 2.

In particular, the spectroscopy cell comprises an outer housing half or part 2 and an inner housing half or part 3, which are arranged essentially opposite. As shown in FIG. 3a, one or more housing connecting areas 13 are formed in each case on opposing inner sides of the outer housing half 2 and the inner housing half 3, to connect the outer and inner housing halves 2, 3 to one another. Upon use of the spectroscopy cell 1 with a bioreactor, i.e., the spectroscopy cell 1 is arranged on the bioreactor and/or connected thereto, in particular connected to an outer wall 101 of the bioreactor, the inner housing half 3 is preferably arranged in contact with the interior of the bioreactor and the outer housing half 2 is arranged on an outer side of the bioreactor. The outer housing half 2 in particular has a (preferably plate-shaped or disk-shaped) connecting region 2b, which extends from the connecting area(s) 13 to the cylinder 43 and enables a stable support of the outer housing half 2 (in particular via the inner housing half 2) on the bioreactor wall 101.

Furthermore, the spectroscopy cell 1 comprises a bioreactor connecting area 8, which is designed for the purpose of connecting the spectroscopy cell 1 to the bioreactor. In particular, the bioreactor connecting area 8 can be formed on the periphery of the spectroscopy cell 1, wherein the bioreactor connecting area 8 can be embodied so it can be welded and/or adhesively bonded and/or screwed and/or detachable on the wall 101 (FIG. 3a) of the bioreactor. A detachable and/or screw-on connection enables the nondestructive separation of the spectroscopy cell 1 from the bioreactor, so that the spectroscopy cell 1 can be reused after a cleaning and/or sterilization.

Figure 1B:
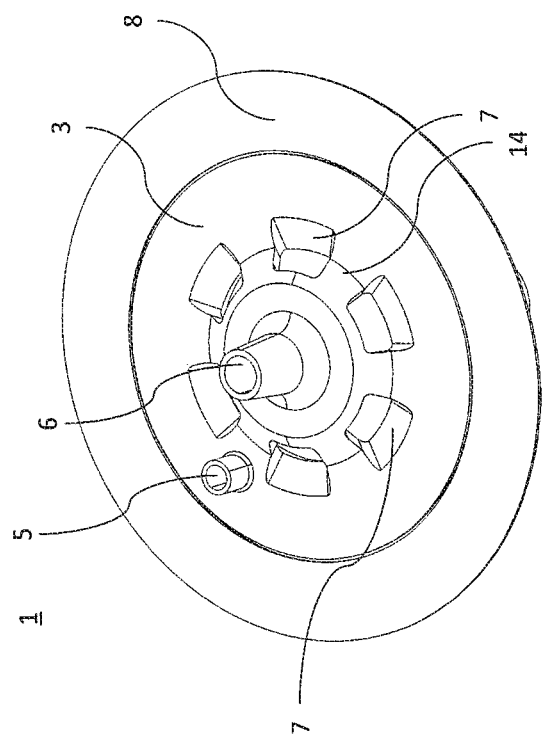
FIG. 1b shows one side of the spectroscopy cell, which is arranged outside the bioreactor container.
Figure 1A:
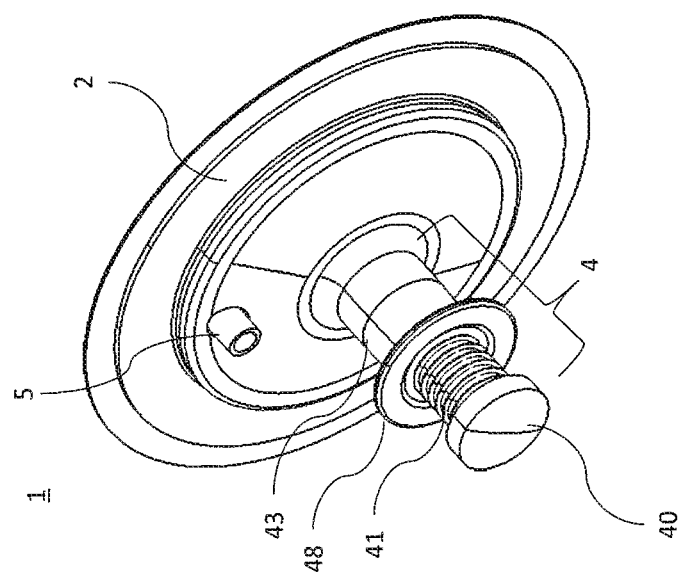
FIG. 1a shows one side of a spectroscopy cell, which is arranged in the interior of a bioreactor container as an example of a container according to one preferred embodiment of the invention.

FIG. 1a furthermore shows a setting element 4 which is arranged on and/or in the outer housing half 2. The setting element 4 is designed for the purpose of setting a distance between a first optical area 10 and a second optical area 11 (see FIG. 3a), which are arranged in the interior of the spectroscopy cell 1. In particular, the setting element 4 comprises a cylinder or plunger 43, which is embodied as substantially hollow cylindrical and extends along a cylinder axis Z. A pressure piston 42 (FIG. 3a) is arranged inside the cylinder 43. The pressure piston 42 is embodied so it is movable and/or displaceable along the cylinder axis Z of the cylinder 43, in order to set a distance between the first optical area 10 and the second optical area 11.

In particular, the cylinder 43 and pressure piston 42 are embodied such that the pressure piston 42 can be moved with as little friction as possible in the cylinder 43. The pressure piston 42 can thus be moved more easily and with lower force application in the cylinder 43 along the cylinder axis Z, which results in better setting ability and/or adjustability and/or operability of the setting element 4 and therefore more precise setting of the distance or relative position between the first optical area 10 and the second optical area 11.

In particular, the cylinder 43 extends from the outer housing half 2 at an angle different from 0° or 180°, in particular substantially orthogonally and away from the inner housing half 3. Furthermore, the cylinder axis Z can be in particular essentially orthogonal to the optical areas 10 and 11.

An operating element 48, which in particular protrudes like a flange from the cylinder 43, is arranged on an end of the cylinder 43 spaced apart from the spectroscopy cell 1. The operating element 48 enables, in conjunction with a pushbutton 40, the convenient operation, in particular setting and/or adjustment of the distance between the first optical area 10 and the second optical area 11. In particular, the operating element 48 is designed such that the operating element 48 is embodied as operable with one hand for the (manual) setting of the distance between the first optical area 10 and the second optical area 11. For example, the operating element 48 can be grasped with an index and middle finger of an operating hand, wherein a thumb of the operating hand presses on the pushbutton 40 arranged on or close to the end of the pressure piston 42.

Furthermore, a compression spring 40 arranged between the pushbutton 40 and the operating element 48 and/or cylinder 43 is designed so as to convey and/or secure the pressure piston 43 in a starting position in a non-actuated state, i.e., in a state in which the pressure piston is not actuated.

Furthermore, the outer housing half 2 and the inner housing half 3 can be embodied as torsionally stiff and/or rigid. It is therefore ensured that the spectroscopy cell 1 does not twist and/or warp upon actuation of the pushing element 40. This ensures a reproducible and reliable setting ability of an optical path length, which is defined by the distance or the relative position between the first optical area 10 and the second optical area 11. In particular, the distance between the first optical area 10 and the second optical area 11 remains constant in the starting position of the pressure piston 42.

Figures 4A, 4B, 4C:
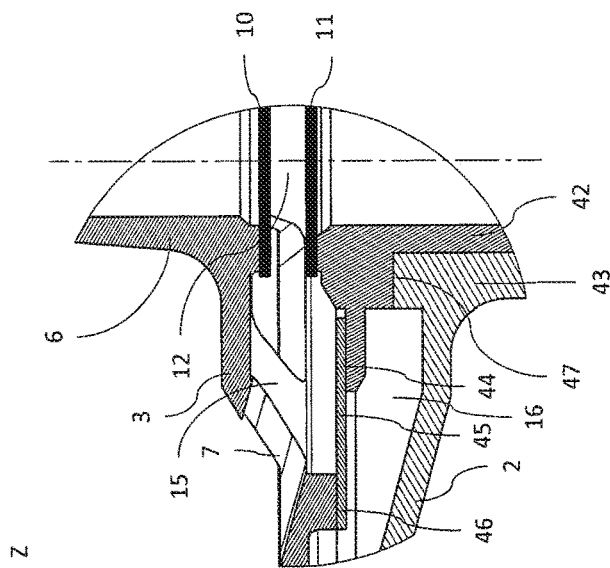
FIG. 4a shows a first detail view of the spectroscopy cell.
FIG. 4b shows a second detail view of the spectroscopy cell and a feedthrough.
FIG. 4c shows a third detail view of the spectroscopy cell.

FIGS. 1a, 1b, and FIG. 4b furthermore show a feedthrough 5, which extends through the outer housing half 2 and the inner housing half 3. The feedthrough 5 can be designed for the purpose of guiding and/or fixing a connecting element 9 (FIG. 3a), wherein the connection between the feedthrough 5 and the connecting element 9 is embodied as leak-tight and/or sealed (for example, by a form fit and/or an adhesive bond and/or weld). Furthermore, the feedthrough is embodied such that a sterility of the interior of the bioreactor is ensured. The feedthrough 5 is in particular embodied in the form of a sleeve in the inner housing half 3 and/or protrudes inward and/or outward in relation to the inner housing half 3. The connecting element 9 is located and/or supported and/or guided by the feedthrough 5. The feedthrough 5 preferably protrudes on the inner housing half 3 such that it protrudes through a recess 2a in the outer housing half 2, so that the connecting element 9 is advantageously supported.

Furthermore, the inner housing half 3 has a fitting 6, which is embodied as hollow-cylindrical in particular, on a side facing away from the outer housing half 2. The fitting 6 can be designed so as to couple and/or connect the connecting element 9 guided by the feedthrough 5 to the inner housing half 3. Furthermore, the fitting 6 can be designed to accommodate an illuminant and/or a detection means D and/or couple and/or connect it to the inner housing half 3

Furthermore, one or more openings 7 are formed on the inner housing half 3, which are in particular arranged essentially symmetrically around a center of the inner housing half 3, in particular symmetrically in the fitting 6. The openings 7 are embodied for the purpose of providing a fluid connection or a channel between the bioreactor container or the interior of the bioreactor and a cavity H located in an interior in the spectroscopy cell 1 (in particular at least partially between the optical areas 10, 11 in their spaced-apart state). The openings 7 are spaced apart from one another by one or more webs 14, wherein in particular the webs 14 are also arranged symmetrically around the center of the inner housing half 3, in particular symmetrically around the fitting 6. In other words, the openings 7 and the webs 14 are arranged on an imaginary circular path around the fitting 6. Furthermore, the webs 14 are designed for the purpose of improving the rigidity of the inner housing half 3. In addition, the openings 7 enable a fluid and/or medium located in the bioreactor to flow and/or drain from the interior of the bioreactor to and/or from the cavity H.

Figure 2:
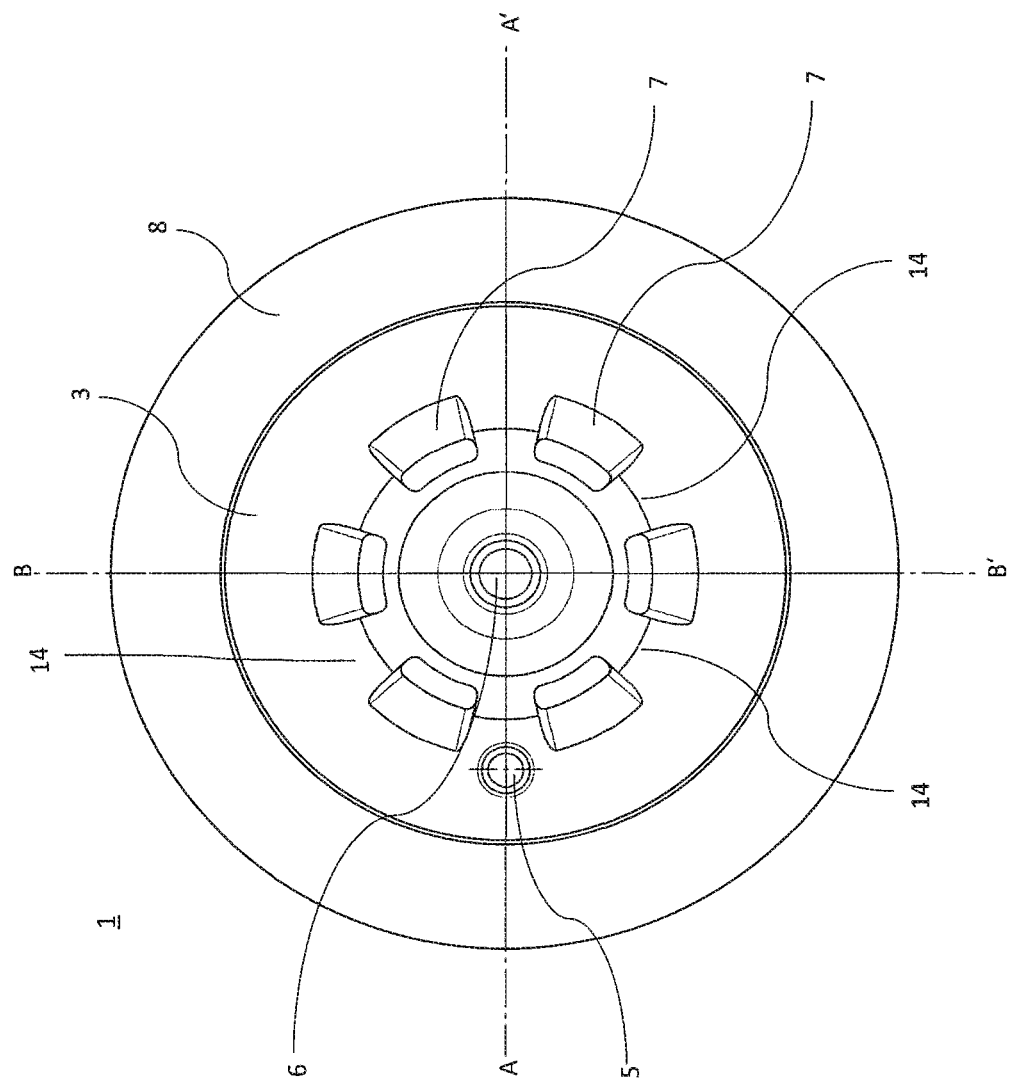
FIG. 2 shows the side of the spectroscopy cell which is arranged in the interior of the bioreactor container.

FIG. 2 shows a top view of the inner housing half 3 of the spectroscopy cell 1. In this case, section line A-A' marks a section through the feedthrough 5 and the fitting 6 and section line B-B' marks a section through two openings 7 and the fitting 6. Reference is explicitly made to the embodiments of the other figures with respect to the further reference signs.

Figure 3B:
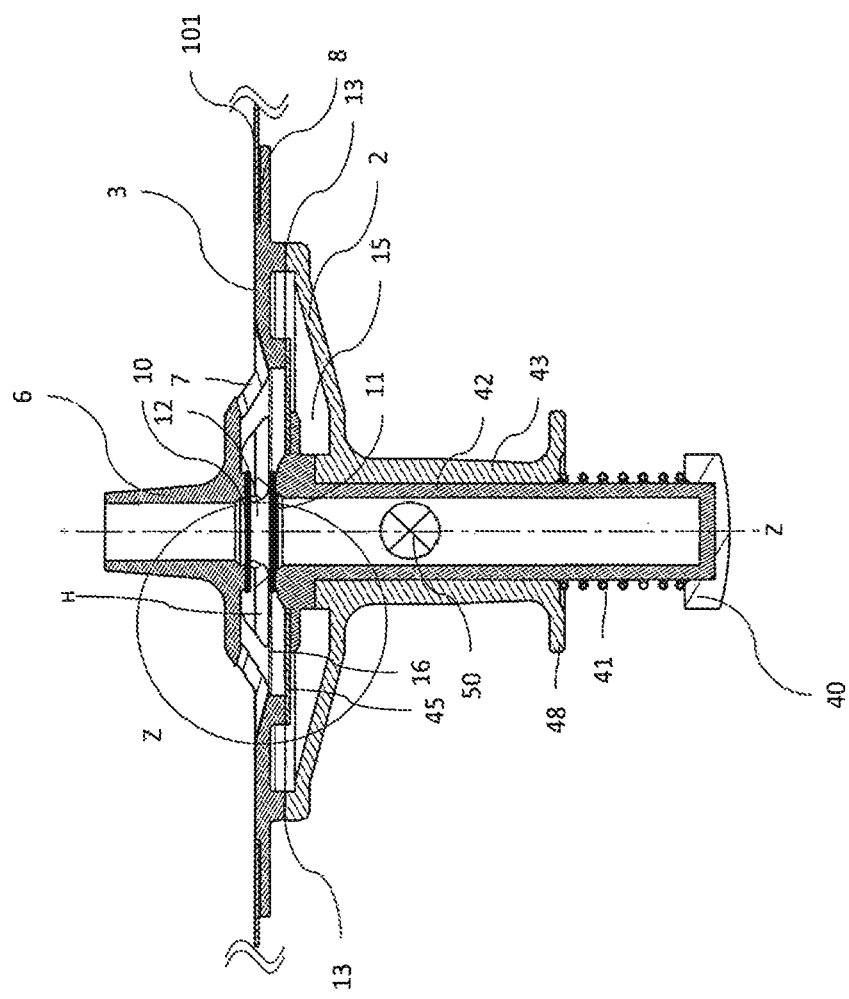
FIG. 3b shows a longitudinal section through the spectroscopy cell along the section line B-B' shown in FIG. 2.

FIGS. 3a and 3b each show various views of the spectroscopy cell, wherein the details on the reference signs X, Y, and Z are shown enlarged in FIGS. 4a, 4b, and 4c, respectively. FIG. 3a shows a longitudinal section through the spectroscopy cell 1 along section line A-A' shown in FIG. 2 and FIG. 3b shows a longitudinal section through the spectroscopy cell 1 along section line B-B' shown in FIG. 2.

The first optical area 10 and the second optical area 11 are arranged in the cavity H formed between the outer housing half 2 and the inner housing half 3 (see also FIG. 4a), wherein the first optical area 10 and the second optical area 11 can be arranged essentially (plane-)parallel in relation to one another in particular.

Furthermore, the first optical area 10 is arranged on the inner housing half 3, in particular on the housing-side opening of the fitting 6.

The second optical area 11 is arranged on or close to a cavity-side end of the pressure piston 42, so that during a movement of the pressure piston 42 along the cylinder axis Z of the cylinder 43, the second optical area 11 is moved in relation to the first optical area 10. The distance or the relative arrangement between the first optical area 10 and the second optical area can thus be set reproducibly by the movement of the pressure piston 42. In particular, the distance between the first optical area 10 and the second optical area 11 can be reduced down to zero.

For the case that the distance between the first optical area 10 and the second optical area 11 is not equal to zero, a specimen space 12 arranged between the first optical area 10 and the second optical area 11 can be filled with a part of the medium and/or fluid located in the bioreactor. This can be from the interior of the bioreactor through the opening(s) 7 into the cavity H.

In particular, the setting element 4 can be designed so as to set the distance between the first optical area 10 and the second optical area 11 manually, for example, by hand, and/or automatically (for example, by means of a stepping motor, by applying an overpressure and/or partial vacuum).

As the detail view shown in FIG. 4c shows, a stop 47 is formed on the cylinder 43 (in particular on a cavity-side end of the cylinder 43 and/or on a cavity-side end face of the cylinder 43), which stop is embodied for the purpose of at least partially flatly contacting a complementary stop area 47 formed on the pressure piston 42. In particular, the stop 47 and the complementary stop area 47 contact one another when the pressure piston 42 is pre-loaded or pressed by a compression spring 41 (as a preferred application means) in a spaced-apart starting position. The optical path length, which is defined by the spacing of the first optical area 10 from the second optical area 11, can be fixed and/or set reproducibly in particular by the torsionally-stiff embodiment of the spectroscopy cell 1 and the starting position formed.

In particular, the first optical area 10 and the second optical area 11 can be embodied as active and/or inactive optical elements. Thus, for example, the optical areas 10, 11 can be embodied as light-transmissive or transparent (i.e., in particular as optical windows) and/or reflective (i.e., in particular as optical mirrors). In particular, an optical area embodied as light-transmissive or transparent can output at least approximately 80% of incident light again (in particular in a spectral range relevant for the measurement) and an optical area embodied as reflective can reflect at least approximately 80% of the incident light (in particular in a spectral range relevant for the measurement). Furthermore, the optical areas can also be embodied as lenticular, for example, to enable focusing of the output light on a specific point, for example, on a detection means D arranged on the optical area and/or on an optical fiber arranged on the optical area.

An illuminant 50 can be arranged inside the cylinder 43 and/or thereon, which is designed for the purpose of inputting or radiating light, in particular electromagnetic radiation suitable for a spectroscopic measurement, into the second optical area 11 in the direction toward the first optical area 10. The input light or radiation traverses the second optical area 11 (embodied in particular as an optical window), possibly medium or fluid located between the two optical areas 10, 11 depending on the spacing of the optical areas 10, 11, and the first optical area 10 (in particular also embodied as an optical window), wherein the light or the radiation exits from the first optical area 10 on a side facing away from the second optical area 11. A detection means D arranged on this side and/or a detection means D coupled to the side via the connecting element 9 is embodied so as to register or detect the spectrum of the output light or the output radiation.

At least one optical fiber, for example, which couples a detection means D and/or illuminant 50 to the fitting 6, can be provided as the connecting element 9. In particular, the connecting element 9 can be embodied as a monomodal or multimodal fiber and/or can comprise multiple fiber bundles.

A determination of a spectrum of a medium or fluid can be carried out in particular as follows:

After the spectroscopy cell 1 is provided in the wall 101 of the bioreactor container of the bioreactor, the optical elements 10, 11 are arranged in a first measuring state (or reference state) by actuating the setting element 4, in which, for example, the distance between the first optical area 10 and the second optical area 11 is reduced (for example, reduced to approximately zero), wherein this distance can be referred to as the (first) reference distance. The reference distance of the two optical areas 10, 11 of the spectroscopy cell 1 can thus be set. For this purpose, in particular the pressure piston 42 is moved in the direction toward the first optical area 10 (for example, manually) against the pre-loading of the compression spring 41, preferably until the first optical area 10 at least partially abuts the second optical area 11. A medium and/or fluid possibly located in the specimen space 12 is preferably at least partially displaced by the pressing together of the two optical areas 10 and 11, wherein the movement of the pressure piston 42 can be performed manually and/or automatically. Therefore, when the optical elements 10, 11 are arranged in the first measuring state (or reference state), i.e., upon arrangement in the (first) reference distance, no medium and/or fluid is preferably located along an optical measuring path between the two optical areas 10 and 11.

A spectroscopic reference measurement is then carried out to ascertain the spectral properties of the first optical area 10 and the second optical area 11. A reference spectrum of the two optical areas 10, 11 can therefore be registered or detected. For this purpose, in particular the electromagnetic radiation suitable for the spectroscopic measurement is input along the optical measuring path (for example, by the illuminant 50) into the second optical area 11 and the radiation exiting at the second optical area 11 (in particular via the connecting element 9) is detected by the detection means D. A reference spectrum resulting therefrom of the first optical area 10 and the second optical area 11 is stored for further processing and/or consideration.

In a further step, the optical elements 10, 11 are arranged in a second measuring state by means of the setting element 4, in which in particular the distance between the first optical area 10 and the second optical area 11 is enlarged, specifically until a specific measuring distance is assumed between the first optical area 10 and the second optical area 11. The measuring distance between the two optical areas 10, 11 can therefore be set, wherein a medium and/or fluid to be studied is arranged between the optical areas 10, 11. The second measuring state (in particular the assumed measuring distance) can be selected such that a spectroscopic measurement following thereon takes place at an optimum optical path length. As soon as the distance between the first optical area 10 and the second optical area 11 increases, the specimen space 12 (at least along the measuring path) fills with the medium and/or fluid to be studied. The setting of the distance can be performed by actuating and/or releasing the setting element 4.

When the optical elements 10, 11 are arranged in the second measuring state and the medium and/or fluid has flowed or drained from the interior of the bioreactor through the opening(s) 7 at least partially into the specimen space 12 and is located in the optical measuring path between the optical areas 10, 11, a measurement spectrum is registered, which comprises or corresponds to the spectral properties of the first optical measuring area 10, the second optical measuring area 11, and the medium and/or fluid located between the two optical measuring areas 10 and 11 along the measuring path. The measurement spectrum of the two optical areas 10, 11 and the medium or fluid located therebetween can therefore be registered or detected. It is to be understood that the registration of the measurement spectrum can take place chronologically and/or positionally from the registration of the reference spectrum. For example, the reference spectrum can be registered at the factory or producer and the measurement spectrum can be registered at the customer or laboratory.

The spectrum of the medium and/or the fluid can then be ascertained or registered. A spectrum of the medium or fluid can therefore be ascertained and/or computed and/or detected based on the reference spectrum and the measurement spectrum. For this purpose, in particular the spectral components and/or effects of the first optical area 10 and the second optical area 11 can be computed out of the measurement spectrum with the aid of the reference spectrum. The spectrum of the medium and/or fluid thus obtained therefore solely corresponds to the spectral properties of the medium and/or fluid. In particular, differences, ratios of measurement and reference spectra or of the vectors of the measurement and reference spectra can be computed out. It is therefore possible to compare spectra of a medium of various bioreactors simply and cost-effectively, since differences of the various optical areas 10 and 11 can be computed out. Furthermore, in the case of a spectroscopic measurement for only one container, a correction of the measurement spectrum is not absolutely necessary as long as the measuring distance is not varied. Drift and/or clogging can advantageously be detected by ascertaining the reference spectrum, for example, by ascertaining changes of the medium at a later measurement point in time in relation to a reference point in time.

However, the measuring method can also be carried out in a modified manner. In particular, the measuring method can provide first registering the measurement spectrum and subsequently the reference spectrum. Furthermore, it is possible to carry out more than one measurement of the reference spectrum and to average the registered reference spectra. It is also conceivable to perform the reference spectrum in a separate method (for example, at the factory) and associate it with the bioreactor as a reference measurement.

Carrying out the spectroscopic method in consideration of the reference spectrum enables increased accuracy of the measurement of the spectral properties of the medium and/or fluid. Furthermore, it enables more cost-effective materials to be used for the production of the optical areas 10 and 11 and costly materials such as sapphire glass and/or quartz glass to be dispensed with in particular. In addition, an optical path length optimum for a spectroscopic measurement can be set, which takes into consideration the wavelength of the input radiation and/or an absorption and/or scattering of different strength of the input light and/or the input radiation by the medium and/or fluid and/or by the optical areas 10 and 11 and/or along the optical measuring path.

According to one particular embodiment, furthermore a membrane 45 embodied or arranged in the interior of the cavity H is provided (see FIGS. 3a, 3b, and 4c). The membrane 45 is connected both to the inner housing half 3 (in particular on at least one inner fastening region 3a) and also to the outer housing half 2 (in particular on at least one outer fastening region 2c) and is designed so as to divide the cavity H into an outer cavity region 15 and an inner cavity region 16. In particular, an interior connecting area 46 is formed, in order to be connected to the membrane 45, on a side of the inner housing half 3 which faces toward the outer housing half 2. The outer fastening region 2c preferably protrudes like a flange from the pressure piston 42 (in particular essentially radially).

Furthermore, a pressure-piston-side connecting area 44 for connecting the pressure piston 42 to the membrane 45 is formed on the cavity-side end of the pressure piston 42. In other words, the membrane 45 is (movably) spanned between the interior connecting area 46 and the pressure-piston-side connecting area 44.

In particular, the membrane 45 is embodied as flexible, so that during a movement of the pressure piston 42, the membrane 45 is carried along and adapts itself to the movement or displacement of the pressure piston 42. The membrane 45 ensures in particular that the specimen space 12 is embodied as movable and/or sealed to the outside and/or sterile.

Furthermore, the outer cavity region 15 can be designed so as to enable an overpressure in the outer cavity region 15. By generating an overpressure in the outer cavity region 15, the membrane 45 can move in the direction toward the inner housing half 3, so that the second optical area 11 moves in the direction of the first optical area 10. In other words, by generating an overpressure in the outer cavity region 15, the distance or a relative position between the first optical area 10 and the second optical area 11 can be set and/or adjusted. In particular, an overpressure fitting can be formed on the outer housing half 2 in order to connect the outer cavity region 15 to a pressure generator, for example, a compressor.

Figure 5B:
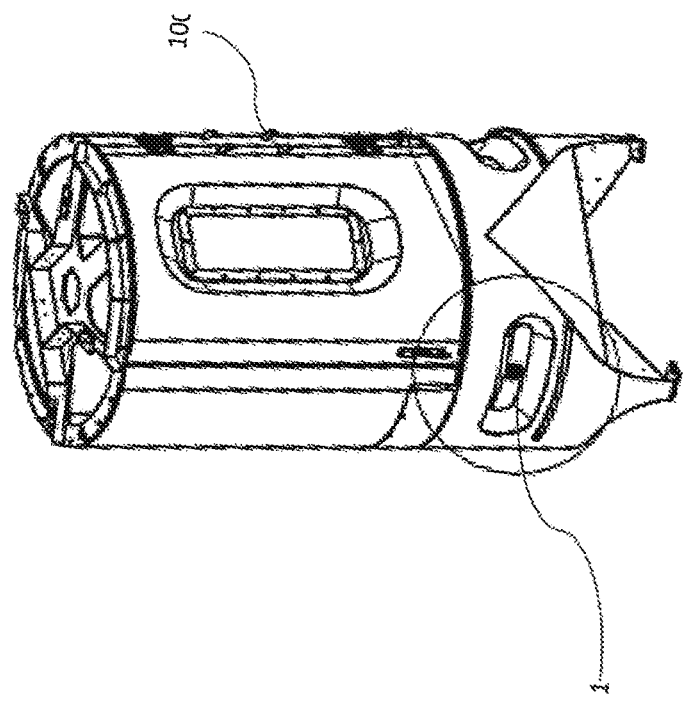
FIG. 5b shows a bioreactor.
Figure 5A:
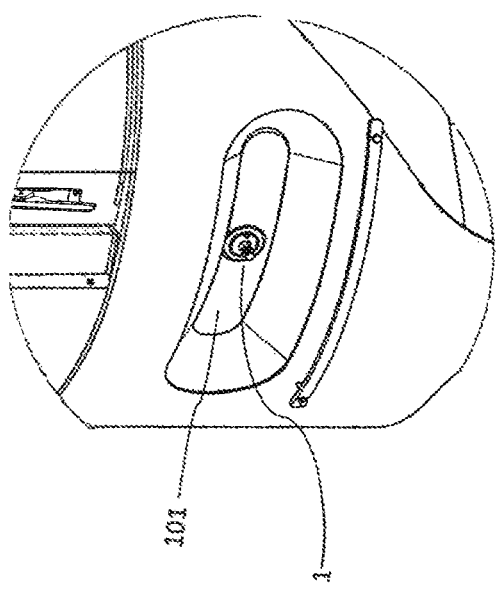
FIG. 5a shows a spectroscopy cell arranged on a bioreactor container.

FIG. 5a shows a spectroscopy cell 1 according to one preferred embodiment, which is arranged in a bioreactor wall 101. FIG. 5b shows a bioreactor container 100 having a spectroscopy cell 1 arranged in the lower region of the bioreactor 100.

According to a further embodiment (not shown) of the invention, an above-described spectroscopy cell 1 can be arranged on a mixing container as a further example of a container or provided therein or thereon. The mixing container can be, for example, a Palletank® (from Sartorius Stedim Biotech GmbH) for LevMixer® (from Pall Corporation) and/or a magnetic mixer for mixing liquid and/or solid components in liquids, for example, for a medium and/or specimen preparation or other process applications. In particular, a Flexel® (from Sartorius Stedim Biotech GmbH) for LevMixer® can advantageously be used with a floating rotor for ultrapure mixing, mixing with low shear, liquid-liquid mixing, homogenization, and/or resuspension. The mixing container can also be used as a Flexel® container for magnetic mixers, which in particular enables strong magnetic coupling of the rotor to ceramic bearings, for powerful thorough mixing with high torque, high speed, high viscosity, and/or concentrated powder dissolution and/or large-volume mixing. In particular, the mixing container can be a Flexel® bag for magnetic mixers, which is employed or used for applications such as buffer and media production, hydration dissolution of hydrophobic powders and/or the product formulation and homogenization of liquids having large volumes, wherein the Flexel® bag for magnetic mixers in particular has a centered magnetic impeller device. In particular, the mixing container can furthermore be a Flexel® bag for LevMixer®, which is employed or used for applications for high-purity mixing, low-shear-force mixing, liquid-liquid mixing, homogenization, and/or resuspension applications, wherein the Flexel® bag for LevMixer® in particular has a magnetic impeller. In all of these applications, one or more properties of the medium inside the mixing container can be measured (also online and/or in real time) by means of the provided at least one spectroscopy cell.

The invention claimed is:

1. A bioreactor and/or mixing container, comprising:
   an outer wall; and
   a spectroscopy cell arranged in the outer wall, wherein the spectroscopy cell comprises:
      a first and second housing part arranged opposite and forming a cavity between the first and second housing part, the first housing part being in contact with an interior of the bioreactor and/or mixing container, wherein one or more housing connecting areas are formed on opposing inner sides of the first and second housing part for connecting the first and second housing part, the first housing part comprising a plurality of openings for providing a fluid connection between the interior and the cavity, the plurality of openings spaced apart from one another by one or more webs;
      a bioreactor connecting area formed on the periphery of the spectroscopy cell and connecting the spectroscopy cell with the outer wall;
      a first optical area arranged at the first housing part;
      a second optical area arranged opposite the first optical area, wherein the first optical area and the second optical area can be set at at least two different distances from one another; and
      a specimen-receiving area located between the first optical area and the second optical area, wherein, at a measuring distance of the at least two different distances, the specimen-receiving area can be filled with a medium from the interior of the bioreactor and/or mixing container through the one or more openings, and
      wherein, for carrying out a spectroscopic measurement, at least one optical area has a light-transmissive embodiment.

2. The container of claim 1, wherein in a reference distance of the at least two different distances, the first optical area and the second optical area abut one another.

3. The container of claim 2, wherein the first optical area and the second optical area are embodied as light-transmissive; or
   wherein the first optical area is embodied as light-transmissive and the second optical area as reflective; or
   wherein the first optical area is embodied as reflective and the second optical area as light-transmissive.

4. The container of claim 2, wherein the spectroscopy cell furthermore comprises:
   an illuminant coupled to the first optical area or second optical area; and
   a detector coupled to the first optical area or second optical area.

5. The container of claim 2, wherein the spectroscopy cell is welded to the container.

6. The container of claim 2, wherein the at least two different distances are settable manually or automatically.

7. The container of claim 2, wherein the first optical area and the second optical area are embodied as light-transmissive.

8. The container of claim 1, wherein the first optical area and the second optical area are embodied as light-transmissive.

9. The container of claim 1, wherein the spectroscopy cell furthermore comprises:
   an illuminant coupled to the first optical area or second optical area; and
   a detector coupled to the first optical area or second optical area.

10. The container of claim 9, wherein the spectroscopy cell furthermore comprises:
    a connecting element that connects the detection means to the first optical area or second optical area; and
    a feedthrough configured to guide the connecting element from an inner side of the container to an outer side of the container.

11. The container of claim 10, wherein the connecting element is an optical fiber.

12. The container of claim 1, wherein the spectroscopy cell is welded to the container.

13. The container of claim 1, wherein the at least two different distances are settable manually or automatically.

14. The container of claim 1, wherein the first optical area and the second optical area are embodied as light-transmissive.

15. A method of performing spectroscopy with a bioreactor and/or mixing container according to claim 1, comprising:
    setting a reference distance of two optical areas of the spectroscopy cell;
    registering a reference spectrum of the two optical areas;
    setting at least one measuring distance between the two optical areas, wherein a medium to be studied is arranged between the optical areas;
    registering at least one measurement spectrum of the two optical areas and the medium located therebetween; and
    ascertaining a spectrum of the medium based on the reference spectrum and the measurement spectrum.

16. The container of claim 1, wherein the first optical area is embodied as light-transmissive and the second optical area as reflective.

17. The container of claim 1, wherein the first optical area is embodied as reflective and the second optical area as light-transmissive.

18. A spectroscopy cell for use with a bioreactor and/or mixing container, comprising:

a first and second housing part arranged opposite and forming a cavity between the first and second housing part, the first housing part for being in contact with an interior of the bioreactor and/or mixing container, wherein one or more housing connecting areas are formed on opposing inner sides of the first and second housing part for connecting the first and second housing part, the first housing part comprising a plurality of openings for providing a fluid connection between the interior and the cavity, the plurality of openings spaced apart from one another by one or more webs;

a bioreactor connecting area formed on the periphery of the spectroscopy cell and for connecting the spectroscopy cell with an outer wall of the bioreactor and/or mixing container;

a first optical area arranged at the first housing part;

a second optical area arranged opposite the first optical area, wherein the first optical area and the second optical area can be set at at least two different distances from one another; and a specimen-receiving area located between the first optical area and the second optical area, wherein, at a measuring distance of the at least two different distances, the specimen-receiving area can be filled with a medium from the interior of the bioreactor and/or mixing container through the one or more openings and wherein, for the carrying out a spectroscopic measurement, at least one optical area has a light-transmissive embodiment.

* * * * *